United States Patent [19]

Cahnmann et al.

[11] Patent Number: 5,169,984
[45] Date of Patent: Dec. 8, 1992

[54] SYNTHESIS AND CHARACTERIZATION OF N-BROMOACETYL-3,3'5-TRIIODO-L-THYRONINE USING HIGH SPEED COUNTERCURRENT CHROMATOGRAPHY

[75] Inventors: Hans J. Cahnmann; Yoichiro Ito, both of Bethesda, Md.

[73] Assignee: The United States of America as represented by the Department of Health and Human Services, Washington, D.C.

[21] Appl. No.: 579,630

[22] Filed: Sep. 10, 1990

[51] Int. Cl.⁵ .................. C07C 229/36; C07C 229/34
[52] U.S. Cl. .................................................. 562/447
[58] Field of Search ........................................ 562/447

[56] References Cited

U.S. PATENT DOCUMENTS 4,430,216  2/1984  Ito .................................. 210/198.2

OTHER PUBLICATIONS

Cheng et al, *J. Biol. Chem.*, 252(17), 6076–6081, 1977.
Matsuura et al, *J. Am. Chem. Soc.*, 81, 871–878, 1959.

*Primary Examiner*—Jose G. Dees
*Assistant Examiner*—B. Frazier
*Attorney, Agent, or Firm*—Lowe, Price, LeBlanc & Becker

[57] ABSTRACT

A method for synthesizing N-bromoacetyl-3,3',5-triiodo-L-thyronine which involves subjecting 3,3', 5-triiodo-L-thyronine to a one-step bromacetylation reaction wherein 3,3', 5-triiodo-L-thyronine and bromoacetyl bromide are refluxed together in a solution of ethyl acetate. After formation the N-bromoacetyl-3,3'-triiodo-L-thyronine is purified by fractionation utilizing high speed countercurrent chromatography. Labeled N-bromoacetyl-3,3'-5-triiodo-L-thryonine may be made by a one-step bromacetylation reaction by reducing either $[^{125}I]T_3$ or $[^{14}C]T_3$ with bromoacetyl bromide.

12 Claims, 6 Drawing Sheets

SYNTHESIS AND CHARACTERIZATION OF N-BROMOACETYL-3,3'5-TRIIODO-L-THYRONINE USING HIGH SPEED COUNTERCURRENT CHROMATOGRAPHY

TECHNICAL FIELD

The present invention relates to highly pure N-bromoacetyl-3,3',5-triiodo-L-thyronine and carrier-free labeled N-bromoacetyl-3,3',5-triiodo-L-thyronine. More particularly, the present invention relates to a method for synthesizing highly pure N-bromoacetyl-3,3',5-triiodo-L-thyronine and preparing carrier-free labeled N-bromoacetyl-3,3',5-triiodo-L-thyronine.

BACKGROUND ART

Labeled N-bromoacetyl-3,3',5-triiodo-L-thyronine (BrAcT$_3$) is widely used as an affinity label for the study of thyroid hormone binding to a variety of receptor sites. This affinity label, as well as its congener N-bromoacetyl-L-thyroxine (BrAcT$_4$), is usually prepared by a two-step reaction: coupling of bromoacetic acid with N-hydroxysuccinimide by means of dicyclohexylcarbodiimide and reaction of the N-hydroxysuccinimide bromoacetate formed with $^{14}$C-labeled or $^{125}$I-labeled 3,3',5-triiodo-L-thyronine (T$_3$) or L-thyroxine (T$_4$). For the synthesis of unlabeled BrAcT$_3$, the second step is carried out with unlabeled T$_3$. However, no physicochemical data have been published to prove unequivocally the identity of the synthesized products and several labeled or unlabeled bands or peaks are always obtained when the crude reaction product is being analyzed by thin layer chromatography (TLC) or by high pressure liquid chromatography (HPLC). It is not clear which one of these bands or peaks represent BrAcT$_3$ or BrAcT$_4$. Accordingly, there exists a need for a simple method for the synthesis of BrAcT$_3$ and of carrier-free BrAc[$^{125}$I]T$_3$.

DISCLOSURE OF THE INVENTION

It is accordingly one object of the present invention to provide a method for synthesizing highly pure N-bromoacetyl-3,3',5-triiodo-L-thyronine.

Another object of the present invention is to provide a one-step reaction for producing highly pure N-bromoacetyl-3,3',5-triiodo-L-thyronine.

A further object of the present invention is to provide a method for synthesizing N-bromoacetyl-3,3',5-triiodo-L-thyronine by a one-step reaction and purifying the N-bromoacetyl-3,3',5-triiodo-L-thyronine utilizing high speed countercurrent chromatography.

A still further object of the present invention is to provide a method for purifying crude N-bromoacetyl-3,3',5-triiodo-L-thyronine.

According to these and other objects, the present invention provides a method for synthesizing N-bromoacetyl-3,3',5-triiodo-L-thyronine which involves subjecting 3,3',5-triiodo-L-thyronine to a one-step bromoacetylation reaction wherein 3,3',5-triiodo-L-thyronine and bromoacetyl bromide are refluxed together in a solution of ethyl acetate.

The present invention further provides a method of purifying crude N-bromoacetyl-3,3',5-triiodo-L-thyronine which comprises subjecting crude N-bromoacetyl-3,3',5-triiodo-L-thyronine to high speed countercurrent chromatography.

BRIEF DESCRIPTION OF THE DRAWINGS

Features and characteristics of the present invention will be described with reference to the following drawings which are given by way of non-limiting examples only, in which.

BEST MODE FOR CARRYING OUT THE INVENTION

The present invention relates to a method for synthesizing highly pure N-bromoacetyl-3,3',5-triiodo-L-thyronine. The method of the present invention involves the bromoacetylation of the thyroid hormone 3,3',5-triiodo-L-thyronine.

According to the present invention a solution of 3,3',5-triiodo-L-thyronine and bromoacetyl bromide in ethyl acetate is refluxed for a period of time to produce the bromoacetylated hormone which is then fractionated by high speed countercurrent chromatography to yield highly pure N-bromoacetyl-3,3',5-triiodo-L-thyronine.

Refluxing time may run from about 5 to 30 minutes or greater depending on the amount of T$_3$ processed. Preferred refluxing times for processing less than 0.01 mmol T$_3$ were about 5 minutes. For processing about 0.01 mmol, optimal refluxing times were about 10 to 15 minutes. For processing amounts of T$_3$ greater than 0.01 mmol, refluxing times of between 15 about to 30 minutes were determined to be preferred. Utilizing the method of the present invention has been found to yield N-bromoacetyl-3,3',5-triiodo-L-thyronine which is up to about 95% pure.

Labeled N-bromoacetyl-3,3',5-triiodo-L-thyronine, i.e., labeled with either [$^{14}$C]T$_3$ or [$^{125}$I]T$_3$, may be formed by the bromoacetylation of [$^{14}$C]T$_3$ or [$^{125}$I]T$_3$. In actual reaction conditions, the [$^{14}$C]T$_3$ or [$^{125}$I]T$_3$ is mixed as a solid with the reaction solution containing the bromoacetyl bromide prior to refluxing. Thus, the labeled N-bromoacetyl-3,3',5-triiodo-L-thyronine may also be produced by a one-step reaction.

The crude reaction product of the bromoacetylation of the 3,3',5-triiodo-L-thyronine is fractionated by means of high speed countercurrent chromatography (HSCCC). The purity of the product was characterized by plasma desorption mass spectrometry (PDMS) and $^1$H nuclear magnetic resonance ($^1$HNMR).

The following non-limiting examples are presented to illustrate features of the present invention which is not meant to be limited thereby. Unless otherwise indicated, percentages are listed by weight.

EXAMPLE 1

BrAcT$_3$ was synthesized according to the following procedure.

A round-bottom flask equipped with a short reflux condenser was used for the processing of more than 0.01 mmol T$_3$. Thus, 0.1 mmol T$_3$ was mixed with 25 ml of ethyl acetate and 500 μl BrAcBr added which causes dissolution of $T_3$. The mixture, after addition of a very small boiling chip, was refluxed for 10 min. The top of the condenser was connected via an empty safety bottle to a wash bottle containing 1M NaOH in 50% ethanol to absorb any escaping BrAcBr or HBr. The reaction mixture was cooled in ice water, then 500 μl of methanol was added to destroy excess BrAcBr.

The reaction mixture was concentrated to a small volume (~0.5 ml) in a rotating evaporator (Buchi Rotovapor R) under reduced pressure (20–30 Torr) using a water bath not exceeding 30° C.

For the processing of amounts of $T_3$ exceeding 0.1 mmol the amounts of reagents and solvent were changed proportionately. For the processing of less than 0.01 mmol $T_3$, including that of carrier-free $[^{125}I]T_3$, the round-bottom flask was replaced with a glass tube fashioned from a 99447 Corning culture tube and a 19/22 joint. In that case, refluxing with a metal block heater (Multi-Blok Heater No. 2090 of Labline Instruments) was reduced to 5 min. In a few experiments, the rotating evaporator was replaced with a concentrator (SpeedVac, Savant) after short precooling of the reaction mixture to avoid bumping. For processing less than 0.01 mmol $T_3$ the amounts of BrAcBr, ethyl acetate, and methanol were always 50 μl, 2.5 ml and 50 μl, respectively, independent of the amount of $T_3$.

To produce carrier-free $^{125}I$-labeled N-bromoacetyl-3,3',5-triiodo-L-thyronine $[^{125}I]T_3$ in solid form is mixed with the reaction mixture. Since $[^{125}I]T_3$ is obtained from the manufacturer as a solution in aqueous propanol, that solvent must be eliminated before bromoacetylation. This is achieved by brief lyophilization for μl amounts or by concentration for ml amounts.

EXAMPLE 2

In this example, the $BrAcT_3$ obtained from Example 1 was fractionated by HSCCC according to the following procedure.

A commercial model HSCCC centrifuge (P.C. Inc., Potomac, Md., USA) was used in this example, although other HSCCC system could be utilized. The apparatus holds a multilayer-coil separation column and a counterweight symmetrically on the rotary frame at a distance of 10 cm from the centrifugal axis of the centrifuge. The column consists of approximately 165 m-long, 1.6 mm-I.D. PTFE tubing with a total capacity of approximately 330 ml. The revolution speed can be regulated up to 1000 rpm with a speed controller.

Two-phase solvent systems composed of hexane/ethyl acetate/methanol/15 mM ammonium acetate (pH 4.0) (1:1:1:1 and 4:5:4:5, v/v) were selected on the basis of partition coefficient values of BrAcT as summarized in Tables I and II below.

TABLE I

Effects of temperature and solute concentration on the partition coefficient* of $BrAcT_3$ in hexane/ethyl acetate/methanol/15 mM ammonium acetate (pH 4.0) (1:1:1:1, v/v/v/v)

|  | 1 mg/ml | 0.1 mg/ml | 0.01 mg/ml | <0.001 mg/ml |
|---|---|---|---|---|
| 10° C. | 2.1 | — | 4.7 | 4.8 |
| 20° C. | 3.0 | 6.0 | 6.0 | — |
| 30° C. | 4.2 | — | 7.4 | 8.1 |

*Numbers in the table denote $K(C_L/C_U)$, i.e., solute concentration in the lower phase divided by that in the upper phase.

TABLE II

Effect of volume ratio of 1-hexane/ethyl acetate/methanol/15 mM ammonium acetate (pH 4.0) on the partition coefficient* of $BrAcT_3$

| hexane/ethyl acetate/methanol/15 mM ammonium acetate | $K(C_L/C_U)$* |
|---|---|
| 5:5:5:5 | 5.7 |
| 4:5:4:5 | 1.5 |
| 3:5:3:5 | 0.21 |

Experimental conditions: temperature: 20° C.; solute concentration: 0.01 mg/ml

*$K(C_L/C_U)$, solute concentration in the lower phase divided by that in the upper phase The solvent mixture was thoroughly equilibrated in a separatory funnel and the two phases were separated shortly before use.

The sample solution (~0.5 ml, ethyl acetate) was first mixed with a proper volume of each of the other solvents (hexane, methanol and 15 mM ammonium acetate) to adjust the phase composition and finally brought to approximately 4 ml by adding equal volumes of the upper and lower phases used for separation.

In each centrifugation, the separation column was first entirely filled with the upper, organic (stationary) phase and the sample solution was injected through the sample port. Then, the apparatus was rotated at 800 rpm while the lower, aqueous (mobile) phase was pumped into the column at a flow rate of 3 ml/min using a metering pump (Milton Roy Minipump, LDC Analytical, Riviera Beach, Fla.). The effluent from the outlet of the column was continuously monitored with a uv monitor (Uvicord S, LKB Instruments, Stockholm, Sweden) at 276 nm and fractionated with a fraction collector (Ultrorac, LKB Instruments) to obtain 3 ml fractions. After the desired peak ($BrAcT_3$) was eluted, the apparatus was stopped and the column contents were fractionated by elution with methanol at a flow rate of 6 ml/min.

HSCCC fractions which were of interest because they showed either high absorbance ($A_{278}$) or high radioactivity were analyzed by PDMS, HPLC, or $^1$HNMR. Depending on the concentration of solute, small aliquots of a single fraction could be used. With very little solute, as for the analysis of carrier-free preparations of $BrAc[^{125}I]T_3$, ten or more fractions had to be combined and concentrated. As expected, unlabeled and labeled $BrAcT_3$ ($A_{278}$ and cpm, respectively) coeluted with identical elution volumes.

The radioactivity of fractions was assessed with a gamma scintillation counter (Auto-Gamma 5000 series, Packard). For the determination of the yield of unlabeled $BrAcT_3$, a small amount (20 μl) of $[3'-^{125}I]T_3$ (Dupont/NEN 100×) was evaporated to dryness and mixed with unlabeled $T_3$. The $BrAc[^{125}I]T_3$ formed upon bromoacetylation served as an internal standard. Furthermore, small duplicate samples (2 μl) of the same $[3'-^{125}I]T_3$ preparation were counted alongside the $BrAc[^{125}I]T_3$ in order to determine the yield as well as mechanical losses.

HPLC analyses were carried out with a Waters chromatograph using a 280-nm absorption detector in conjunction with an absorption recorder (Omniscribe, Houston Instrument Co.) and a fraction collector (FRAC-100, Pharmacia). Conditions were: 15-cm Nova $C_{18}$ column; solvent A, 15 mM ammonium acetate, pH 4.0, prepared by adding acetic acid to an aqueous solution of 1.2 g ammonium acetate until pH 4.0 is reached and bringing the solution to a total volume of 1L with H₂O; solvent B, acetonitrile; linear gradient (started 1 min after injection), 20–60% B in 40 min; flow rate, 1 ml/min; sensitivity, 0.1 absorbance units/chart width in most instances and 0.2 or 0.5 absorbance units/chart width in some cases. Higher sensitivities (0.05 or 0.01) were required for the detection of carrier-free $BrAc[^{125}I]T_3$.

$T_4$ ($10^{-3}$M) was always used as an internal standard. With a sensitivity setting of 0.1, 5 μl were injected together with the sample.

PDMS spectra were measured using a modified spectrometer. An accelerating voltage of 10 kV was used with a flight path of 42 cm. Samples were electrosprayed onto aluminized mylar films and spectra were allowed to accumulate for at least 1 hour before processing (Perkin-Elmer 3220 data system).

Ultraviolet spectra were determined with a spectrophotometer (Cary 219) using quartz cells with a 1-cm light path.

The melting point of $BrAcT_3$ was taken using a hot stage microscope (Kofler).

In the case of $BrAcT_3$ the purification by HSCCC was found to be dependent not only on temperature (a generally observed phenomenon), but also on solute concentration (nonlinear isotherm). Table I shows the effect of temperature and concentration, using the solvent systems hexane/ethyl acetate/methanol/15 mM aqueous ammonium acetate, pH 4.0 (volume ratio 1:1:1:1). As shown in tables I and II, the partition coefficient K ($C_L/C_U$) (see footnote to Tables I and II) increases with increasing temperature and with decreasing concentration. The dependence on concentration (Table I) was attributed to reversible aggregation. The table shows that the solvent system used is appropriate for a $BrAcT_3$ concentration of 1 mg/ml, but results in excessive K values for lower concentration. This solvent system was used for concentrations of 1 mg/ml and greater.

For use with much lower solute concentrations, including those prevailing when carrier-free $BrAc[^{125}I]T_3$ is to be purified, the effect of changing solvent volume ratios on K values was investigated (Table II).

The ethyl acetate and aqueous ammonium acetate buffer ratios within the total solvent system were kept constant, but the volumes of hexane and of methanol were gradually decreased. A decrease of the hexane volume results in an increase of polarity of the solvent system, while a decrease in methanol volume serves mainly to maintain the interfacial tension between the two phases. A decrease in interfacial tension, which would occur if the methanol volume were kept constant, would result in loss of peak resolution due to a decrease of the volume of the stationary (organic, upper) phase retained in the column. For the purification of $BrAcT_3$ present in low concentration (0.01 mg/ml or less) including carrier-free $BrAc[^{125}I]T_3$ a hexane/ethyl acetate/methanol/15 mM ammonium acetate volume ratio of 4:5:4:5 was chosen because Table II shows that this ratio results in a K value not too far from unity.

Figure 1A:
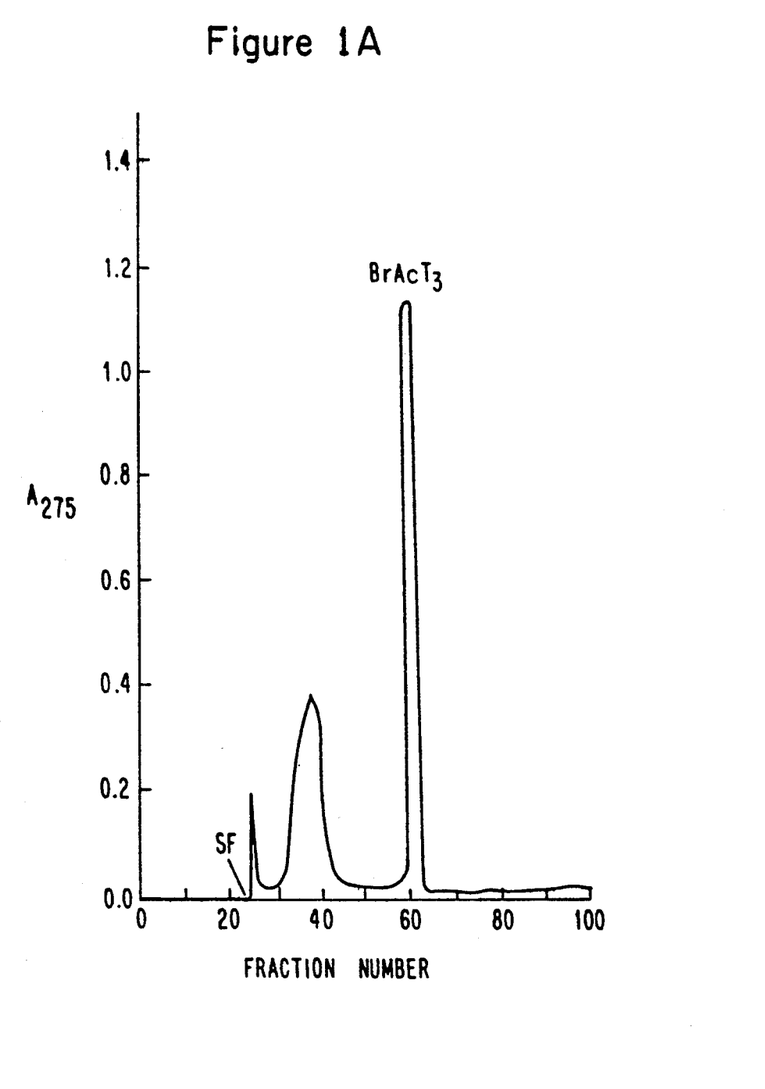
FIGS. 1A and 1B show chromatograms (HSCCC) of crude BrAcT$_3$ obtained by reacting T$_3$ with BrAcBr.
Figure 1B:
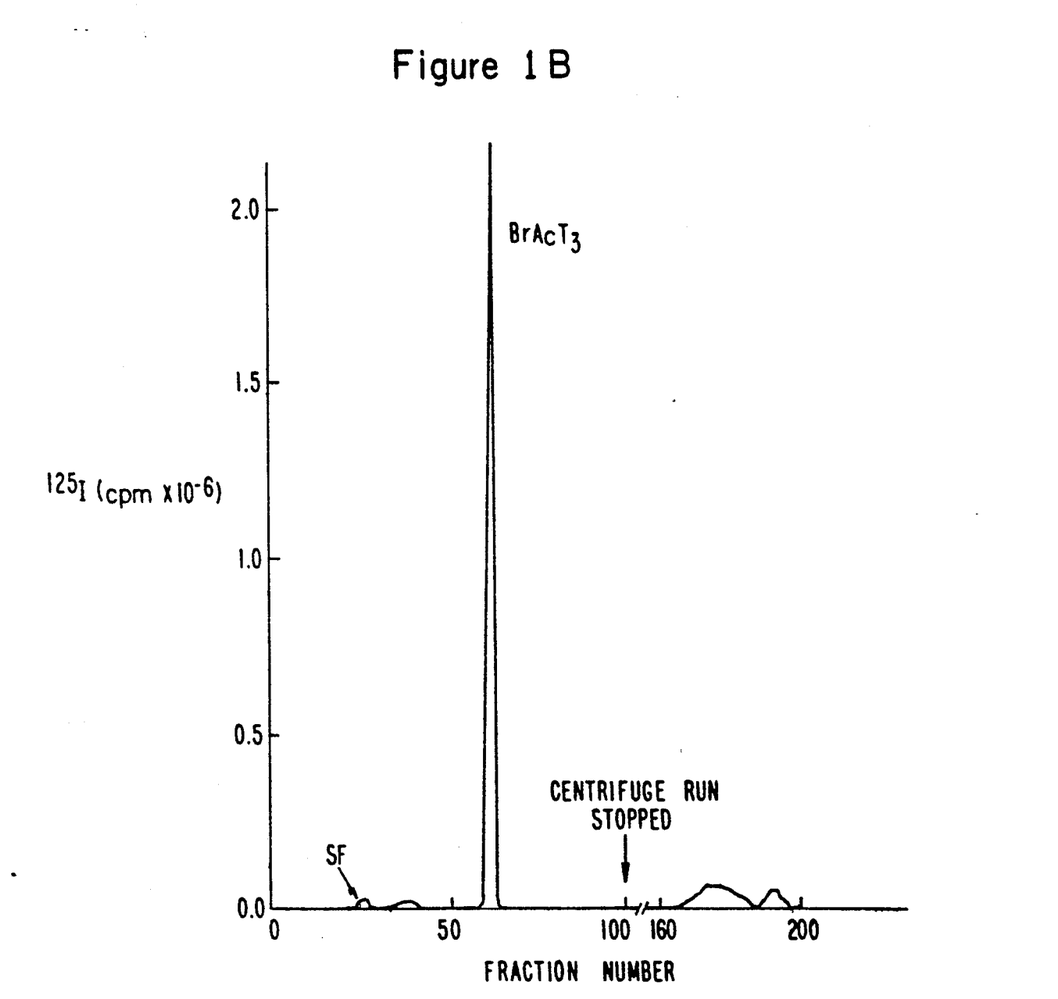

FIGS. 1A and 1B shows chromatograms (HSCCC) of crude $BrAcT_3$ obtained by reacting $T_3$ with BrAcBr. Chromatograms were monitored by uv absorbance (A) and by radioactivity of a $^{125}$I-labeled internal marker (B). Parameters of the HSCCC included: solvent system, hexane/ethyl acetate, methanol, 15 mM ammonium acetate, pH 4.0 (1:1:1:1); mobile phase, lower (aqueous) phase; flow rate, 3 ml/min; 3 ml fractions; revolution, 800 rpm; retention of stationary phase, 77% of column capacity (330 ml); maximal column pressure, 65 psi.

FIGS. 1A and 1B show absorbance (276 nm) and radioactivity profiles in HSCCC, respectively. the yield of $BrAcT_3$ in this and similar bromoacetylations, as described above was about 54%. The yield of $BrAcT_3$ was somewhat lower when very small amounts of $T_3$ (<0.01 mmol) were used.

Figure 2A:
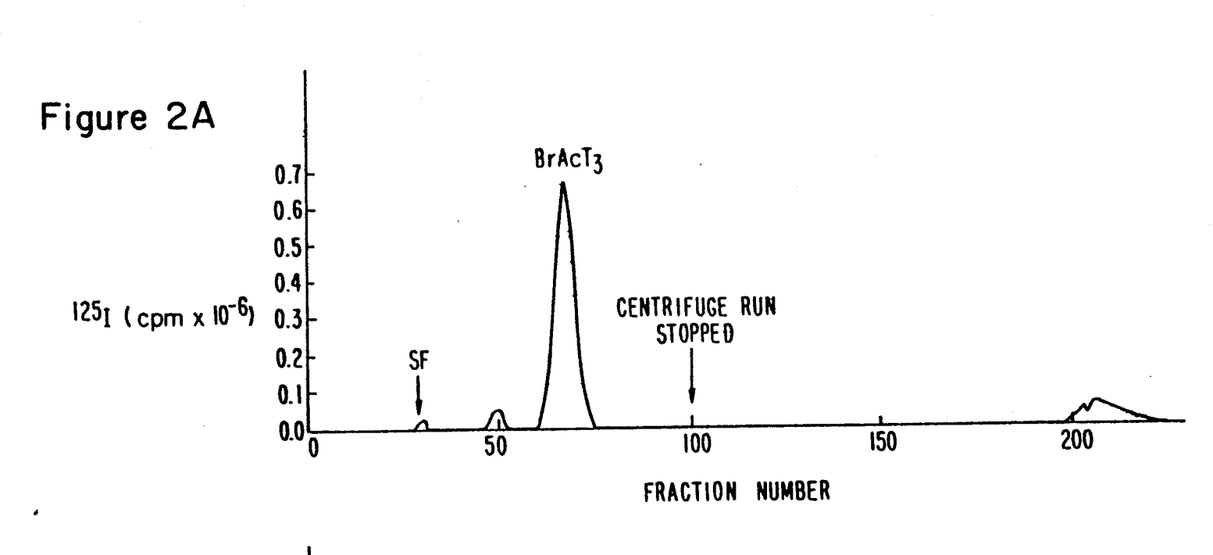
FIGS. 2A and 2B show chromatograms (HSCCC) of crude $^{125}$I-labeled BrAcT$_3$ obtained by reacting carrier-free [$^{125}$I]T$_3$ with BrAcBr.
Figure 2B:
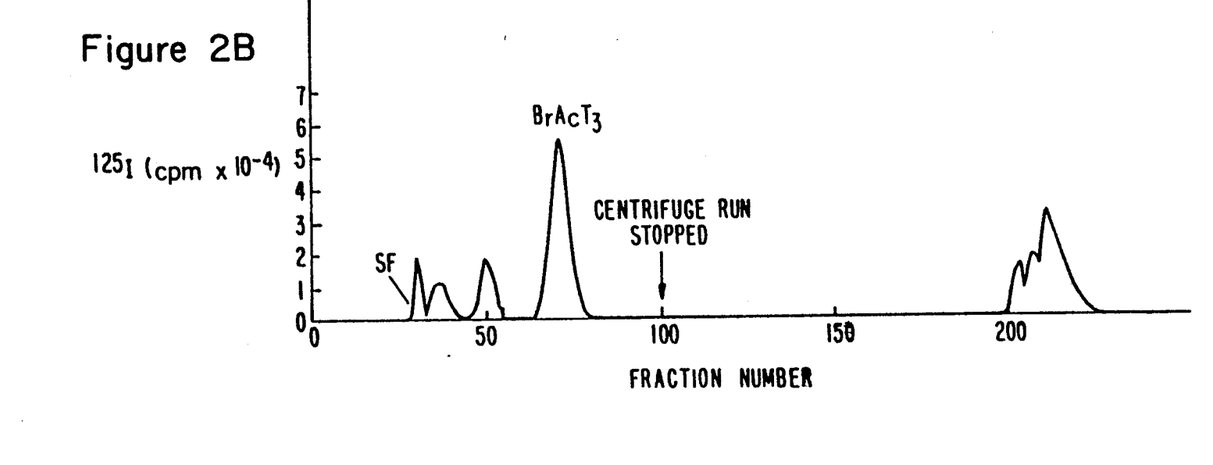

FIGS. 2A and 2B show chromatograms (HSCCC) of crude $^{125}$I-labeled BrAcT obtained by reacting carrier-free $[^{125}I]T_3$ with BrAcBr. Chromatograms were monitored by radioactivity. In FIG. 2A the sample was freshly prepared while in FIG. 2B the sample was stored for 4.2 months in ethyl acetate at −20° C. The parameters of the HSCCC were as follows: solvent system, hexane/ethyl acetate/methanol/15 mM ammonium acetate, pH 4.0 (4:5:4:5). Other conditions were the same as in FIGS. 1A and 1B.

Derivatization of carrier-free $[3'-^{125}I]T_3$ (FIG. 2A) resulted in yields of 30–40%. This lower yield is presumably due to mechanical losses such as adsorption of $BrAcT_3$ on the Teflon wall of the HSCCC column and to more pronounced side reactions when only trace amounts of $T_3$ are being processed.

PDMS of the byproduct eluting from the column at fractions 37–39 in FIG. 1 indicated that it consists largely of acetyl-$T_3$ presumably formed by aminolysis of ethyl acetate. Similarly, PDMS of the very hydrophobic material eluting in fractions 170–190 (FIG. 1B) and consisting of a mixture of two or more compounds strongly suggests that one of these is $BrAcT_3$ ethyl ester presumably arising from transesterification of $BrAcT_3$ with ethyl acetate. While acetyl-$T_3$ cannot be directly linked covalently to $T_3$ receptors, $BrAcT_3$ ethyl ester should be able to react with nucleophiles in $T_3$ receptors to establish a covalent bond. The amounts of all byproducts increase with refluxing for much shorter periods of time results in incomplete conversion of $T_3$ to $BrAcT_3$. The small peak at the solvent front in FIGS. 1A and 1B is caused by unreacted $T_3$.

A sample of N-acetyl-$T_3$ obtained as a byproduct in HSCCC (fraction 31) was checked against the PDMS pattern of authentic N-acetyl-$T_3$. It showed $(M+H)^+$, (MNa), and $(M+2Na-H)^+$ ions at m/z 691, 714 and 736, i.e., c.a. 79 amμ less ($-Br+H$) than $BrAcT_4$. Ions are also present at m/z 588 and 610 for the losses of HI from the sodiated species.

A sample apparently containing $BrAcT_3$ ethyl ester (fraction 136) shows $(M+Na)$ and $(M+H)^+$ ions at m/z 824 and 801, i.e., 28-29 amμ higher than the corresponding ions at $BrAcT_4$. Ion A (FIG. 3) is also present at m/z 606 showing that the excess mass is confined to the carboxyl group, presumably as the ethyl ester. This is in agreement with its long retention by the nonpolar (organic) phase in HSCCC.

Figure 3:
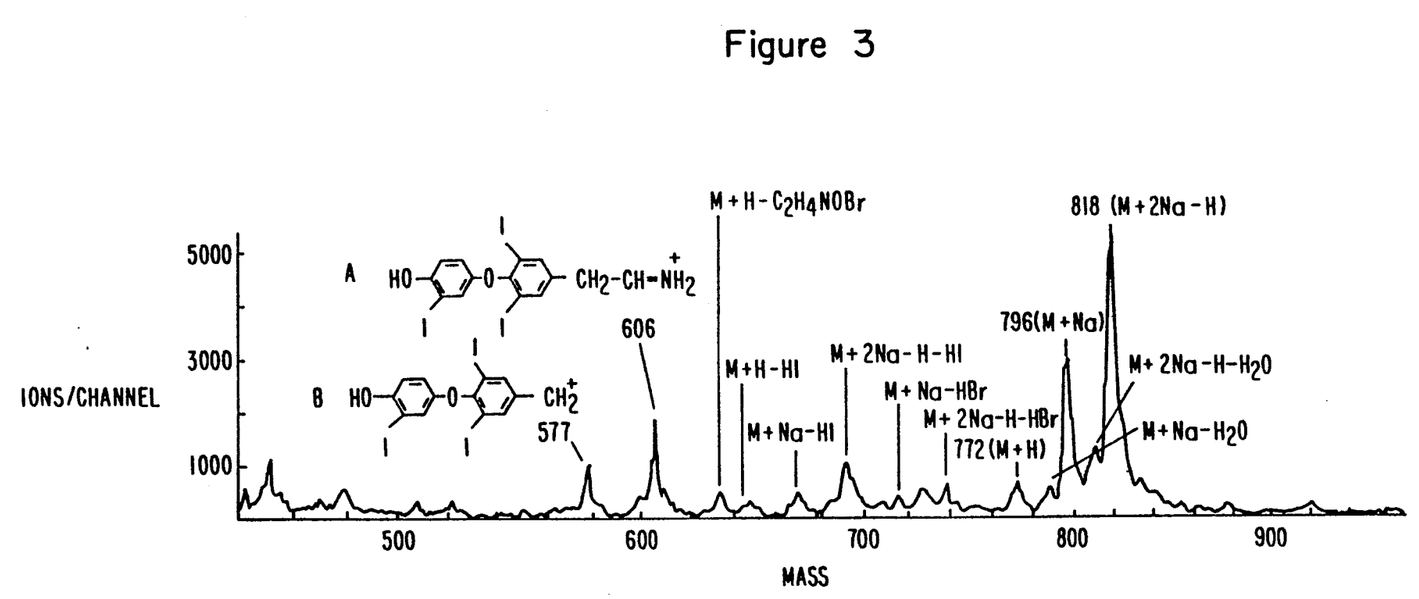
FIG. 3 shows mass spectrum (PDMS) of BrAcT$_3$.

The main HSCCC peak was clearly identified as $BrAcT_3$ by PDMS as well as by HNMR. It is a very narrow peak when milligram amounts of $T_3$ are being processed (fractions 59–63 in FIGS. 1A and 1B) and broader when carrier-free $T_3$ is being used (fractions 61–74 in FIG. 2a). A sample of $BrAcT_3$ purified by HSCCC (fraction 37) produced the mass spectrum shown in FIG. 3. As is common for acidic and hydroxylic groups in PDMS, the most abundant peak in the molecular weight region at m/z 818 (calc. 816.9) corresponds to the $(M+2Na=H)^+$ ion with smaller peaks for the $(M+H)^=$ and $(M+Na)^+$ ions at m/z 772 and 796. Losses from all three of these species of HBr and HI are evident while the $(M+H)^+$ ion also loses formic acid and bromoacetamide to give the corresponding styrene ions. Benzylic cleavage (ion A, FIG. 3) and formation of the imine ion B, FIG. 3, are also prominent. At lower masses the only important ions are at m/z 173 and 219 due to $(Na_2I)^+$ and the phenolic ring, respectively. Ions at m/z 322, 363, and 413 were variable in intensity and may represent impurities.

The NMR spectrum of a second sample of the same retention volume (fraction 50) in deuteromethanol showed a quartet at $\delta$ 3.83 (J=11.2) from geminal coupling of the hydrogens of the $CH_2$ of the N-bromoacetyl group, the asymmetry arising from the proximity of the alpha amido acid carbon. Likewise, the two benzylic protons were seen at $\delta$ 2.95 and 3.24 (J=12.8) coupled further to the alpha proton at $\delta$ ca. 4.65 (J=8.8 and 4.8) as shown by decoupling.

When a preparation of crude carrier-free BrAcT$_3$ (prior to HSCCC) was kept in ethyl acetate in a well-sealed container at $-20°$ C. for over four months, partial decomposition of BrAcT$_3$ took place as a comparison of FIGS. 2A and B shows, but even after this period of time pure BrAcT$_3$ can still be obtained in somewhat reduced yield by HSCCC.

For the resolution of crude BrAcT$_3$, HSCCC has been found to be far superior to TLC and also to HPLC. For example, a main disadvantage of TLC is that several consecutive runs are required to obtain a fairly pure BrAcT$_3$ preparation and this causes considerable losses due to irreversible adsorption to the silica gel. It is difficult to obtain reasonable amounts of unlabeled BrAcT$_3$ as required for competition studies and as reference material.

When crude preparations of BrAcT$_3$ were analyzed by HPLC, the BrAcT$_3$ peak was always accompanied by a satellite peak eluting immediately before the main peak. the two peaks were not resolved when preparative HPLC was used. The HSCCC peak material eluted in fractions 37-39 in FIGS. 1A and 1B produced an HPLC peak having a retention time identical to that of the satellite peak (not shown). Crude BrAcT$_3$ preparations obtained by a conventional two-step method mentioned above also showed in HPLC a satellite peak with identical retention time. Therefore, the satellite material presumably consists at least in part of acetyl-T$_3$.

Figure 4A:
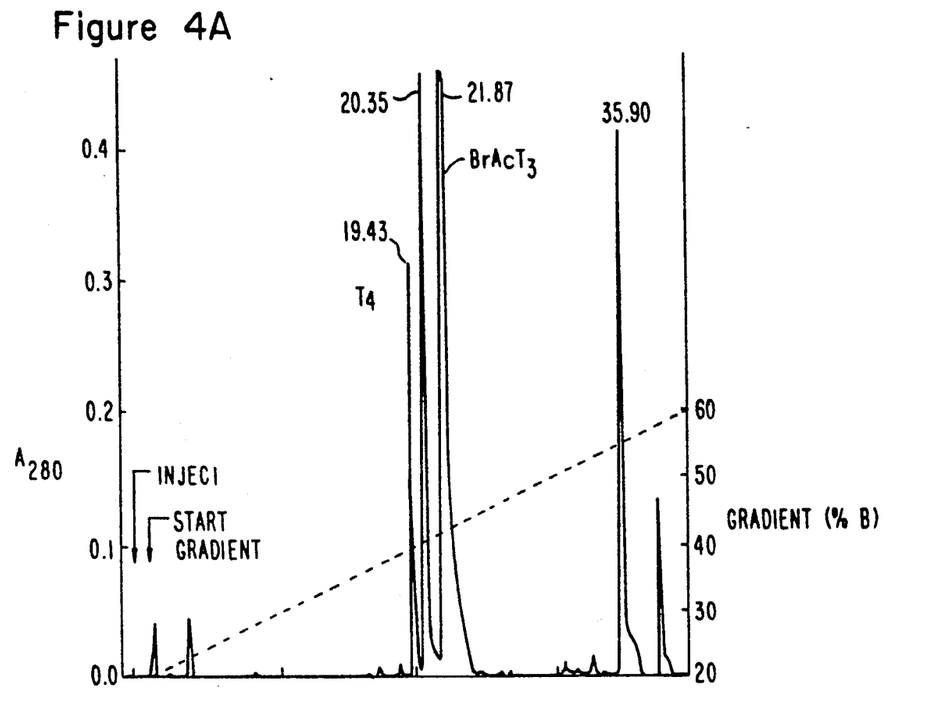
FIGS. 4A and 4B show HPLC of crude BrAcT$_3$ (prior to HSCCC, (FIG. 4A) and of purified BrAcT$_3$, HSCCC fraction 61 (FIG. 4B).
Figure 4B:
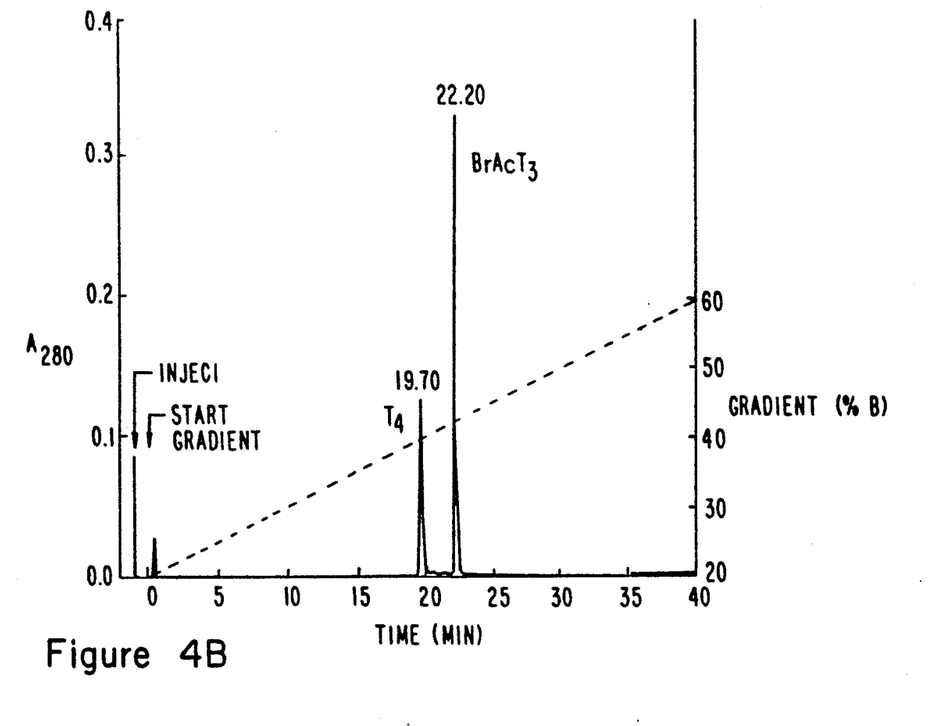

FIGS. 4A and 4B show HPLC of crude BrAcT$_3$ (prior to HSCCC, (FIG. 4A) and of purified BrAcT$_3$, HSCCC fraction 61 (FIG. 4B). A Waters chromatograph having a 15-cm C$_{18}$ Nova column (Waters) was utilized with the following parameters: flow rate, 1 ml/min; sensitivity, 0.5 absorbance units/chart width; solvents, 15 mM ammonium acetate, pH 4.0 (FIG. 4A) and acetonitrile (FIG. 4B); linear gradient (started 1 min after injection), 20-60% B in 40 min. An internal standard ($10^{-3}$M T$_4$, 20 $\mu$l for FIG. 4A and 10 $\mu$l for FIG. 4B) was injected together with 2 $\mu$l of the sample.

HPLC elution patterns of crude BrAcT$_3$, prior to HSCCC) and of pure BrAcT$_3$ (after HSCCC, fraction 61) are shown in FIGS. 4A and 4B. Pure BrAcT$_3$ eluted very reproducibly 2.5 min after T$_4$ (FIG. 4B). The 35.90-min peak in 4A and the smaller peak with still longer retention time presumably correspond to two components of the very hydrophobic HSCCC double peak (FIG. 1B, fractions 166-196). T$_3$ eluted before T$_4$ (not shown).

In earlier experiments TLC (silica gel plates, acetic acid/ethyl acetate, 1:9) was used, while HPLC was used in some later experiments.

Figures 5A, 5B:
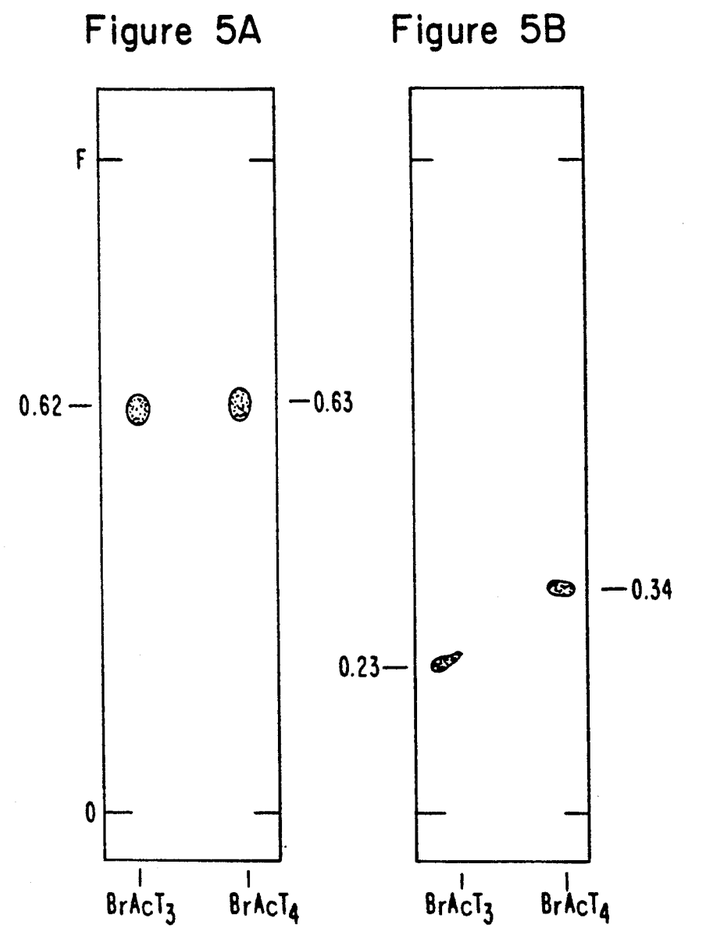
FIGS. 5A and 5B show TLC of BrAcT$_3$ and of BrAcT$_4$ in two solvent systems.

FIGS. 5A and 5B show TLC of BrAcT$_3$ and of BrAcT$_4$ in two solvent systems: acetic acid/ethyl acetate (1+9 vols) (FIG. 5A) and acetic acid/methanol/chloroform (1:4:45), freshly prepared (FIG. 5B). HSCCC fraction 61; Whatman K6F silica gel plates, 5×20 cm.

Before switching to HSCCC in conjunction with HPLC, the solvent system shown in the legend to FIG. 5B was utilized because it has a superior resolving power. FIGS. 5A and B are the chromatograms of HSCCC-purified BrAcT$_3$ and BrAcT$_4$ in the two solvent systems. The R$_f$ values shown in FIG. 5 are reproducible only with the same type of TLC plates (Whatman K6F, 250 $\mu$m layer); R$_f$ values obtained with preparative plates (Whatman PLK5F, 1000 $\mu$m layer) are considerably lower. Also the presence of a large amount of impurity changes R$_f$ values.

Pure BrAcT$_3$ has a melting point of 217.5°-218.5° C. with apparent decomposition since the melt is brownish, while the BrAcT$_3$ used was a white solid material. It was obtained by concentrating HSCCC fraction 67 to one half of its volume in a concentrator (SpeedVac Savant) and then precipitating BrAcT$_3$ by adding water. The precipitated material was collected by filtration, dried in a vacuum desiccator, and stored at room temperature in an amber container.

The uv absorption spectrum of this 94.4% pure BrAcT$_3$ (HPLC) in 0.01M NaOH containing 0.5% ethanol, showed the typical two peaks of 3'-iodo-4'-hydroxydiphenyl ethers having a side chain in position 1. One is at 320 nm (=5500), the other one at 225 nm (=49300). In an acidic solvent (lower phase of HSCCC solvent 1:1:1:1) and in 1-butanol the higher wavelength peaks were at 297 and 299 nm, respectively. 3,3',5'-triiodo-L-thyronine ("reverse T$_3$") has $_{max}$ at 322 nm (=6150) in 0.01M NaOH (unpublished data).

It has been concluded from the above investigations that HSCCC is the method of choice for the purification of crude BrAcT$_3$, conveniently prepared by a simple one-step bromoacetylation of T$_3$.

Although the invention has been described with reference to particular means, materials and embodiments, from the foregoing description, one skilled in the art can easily ascertain the essential characteristics of the present invention and various changes and modifications may be made to adapt the various usages and conditions without departing from the spirit and scope of the present invention as described in the claims which follow.

We claim:

1. A method for synthesizing N-bromoacetyl3,3',5-triiodo-L-thyronine which comprises subjecting 3,3',5-triiodo-L-thyronine to a one-step bromoacetylation reaction with bromoacetyl bromide wherein after synthesis, said N-bromoacetyl-3,3',5-triiodo-L-thyronine is subjected to high speed countercurrent chromatography fractionation to obtain a product which consists essentially of N-bromoacetyl-3,3',5-triiodo-L-thyronine.

2. A method for synthesizing N-bromoacetyl-3,3',5-triiodo-L-thyronine according to claim 1, wherein said high speed countercurrent chromatography utilizes a solvent system comprising hexane/ethyl acetate/methanol/15 mM ammonium acetate having a pH of about 4.0.

3. A method for synthesizing N-bromoacetyl-3,3',5-triiodo-L-thyronine according to claim 2, wherein said hexane/ethyl acetate/methanol/15 mM ammonium acetate are present in a ratio of 1:1:1:1 by volume.

4. A method for synthesizing N-bromoacetyl-3,3',5-triiodo-L-thyronine according to claim 2, wherein said hexane/ethyl acetate/methanol/15 mM ammonium acetate are present in a ratio of 4:5:4:5 by volume.

5. A method for synthesizing N-bromoacetyl-3,3',5-triiodo-L-thyronine according to claim 2, wherein said high speed countercurrent chromatography is conducted at a temperature in the range of from about 10° to about 30° C.

6. A method for synthesizing labeled N-bromoacetyl-3,3',5-triiodo-L-thyronine according to claim 1, further comprising labeling said N-bromoacetyl-3,3',5-triiodo-L-thyronine by conducting said bromoacetylation reaction in the presence of a labeled 3,3',5-triiodo-L-thyronine.

7. A method for synthesizing labeled N-bromoacetyl3,3',5-triiodo-L-thyronine according to claim 6, wherein said 3,3',5-triiodo-L-thyronine is labelled with an element selected from the group consisting of $^{125}$I, $^{14}$C, and mixtures thereof.

8. A method of purifying crude N-bromoacetyl-3,3',5-triiodo-L-thyronine which comprises subjecting crude N-bromoacetyl-3,3',5-triiodo-L-thyronine to high speed countercurrent chromatography to obtain a product which consists essentially of N-bromoacetyl-3,3',5-triiodo-L-thyronine.

9. A method of purifying crude N-bromoacetyl-3,3',5-triiodo-L-thyronine according to claim 8, wherein said high speed countercurrent chromatography utilizes a solvent system comprising hexane/ethyl acetate/methanol/15 mM ammonium acetate having a pH of about 4.0.

10. A method of purifying crude N-bromoacetyl-3,3',5-triiodo-L-thyronine according to claim 9, wherein said hexane/ethyl acetate/methanol/15 mM ammonium acetate are present in a ratio of 1:1:1:1 by volume.

11. A method of purifying crude N-bromoacetyl-3,3',5-triiodo-L-thyronine according to claim 9, wherein said hexane/ethyl acetate/methanol/15 mM ammonium acetate are present in a ratio of 4:5:4:5 by volume.

12. A method of purifying crude N-bromoacetyl-3,3',5-triiodo-L-thyronine according to claim 9, wherein said high speed countercurrent chromatography is conducted at a temperature in the range of from about 10° to about 30° C.

* * * * *

UNITED STATES PATENT AND TRADEMARK OFFICE
CERTIFICATE OF CORRECTION

PATENT NO. : 5,169,984

DATED : December 8, 1992

INVENTOR(S) : Cahmann et al

It is certified that error appears in the above-identified patent and that said Letters Patent is hereby corrected as shown below:

On title page, Item [57]: Abstract, line 1, please change "5-trii-" to --5-tri--; line 2, change "odo-L-thyronine" to --iodo-L-thyronine--; line 2, please change "3',5-trii-" to --3',5-tri--; line 3, please change "odo-L-thyronine" to --iodo-L-thyronine--; line 6, after "formation" please add --,-- and further change "3'-trii" to --3',5-tri--; line 7, please change "odo-L-thyronine" to --iodo-L-thyronine--; line 9, please change "3'-5" to --3',5--; and on line 10 please change "reducing" to --reacting---.

Column 1, line 2, please change "3,3'5" to --3,3',5--; column 2, line 11, please change "BrAcBr." to --BrAcBr; freshly prepared (2A) and after storage for 4.2 months (2B)--; line 17, please change "systems." to --systems; acetic acid/ethyl acetate (1:9) (5A) and acetic acid/methanol/chloroform (1:4:45) (5B).--;

Column 3, line 1, please change "BrAcBr added which causes" to read as follows --BrAcBr was added to cause--; line 12 after "bath" please add --at a temperature--; line 30,

UNITED STATES PATENT AND TRADEMARK OFFICE
CERTIFICATE OF CORRECTION

PATENT NO. : 5,169,984
DATED : Decmeber 8, 1992
INVENTOR(S) : Cahmann et al

It is certified that error appears in the above-identified patent and that said Letters Patent is hereby corrected as shown below:

after "$T_3$" please add a space before the word "in"; in line 43, please change "system" to --systems--; and in line 55, please change "BrAcT" to --$BrAcT_3$--.

Column 4, line 19 after "composition and" please add --was--.

Column 5, line 5, please delete "20"; line 13, please change "electros-" to --electro--; line 14 please change "prayed" to --sprayed--; and at line 40, please delete "[$^1$-"; line 41, please change "25I]" to --[$^{125}$I]--.

Column 6, line 4, please change "respectively. the" to --respectively. The--; line 10 please change "BrAcT" to --$BrAcT_3$--.

Column 7, line 4, please change "ion B, FIG.3" to --(ion B, FIG. 3)--; line 22, after "son" delete "of" and add --between--; further on line 22, please change "B" to --2B--; and in line 61, please change "4A" to --FIG. 4A--.

UNITED STATES PATENT AND TRADEMARK OFFICE
CERTIFICATE OF CORRECTION

PATENT NO. : 5,169,984
DATED : December 8, 1992
INVENTOR(S) : Cahmann, et al

It is certified that error appears in the above-indentified patent and that said Letters Patent is hereby corrected as shown below:

Column 8, line 10, please change "B" to --5B--; and in line 50, please change "N-bromoacetyl3," to -- N-bromoacetyl-3,--.

Column 9, line 17, please change "bromoacetyl3,3'5-" to -- bromoacetyl-3,3',5- --.

Signed and Sealed this

First Day of March, 1994

BRUCE LEHMAN

Attesting Officer     Commissioner of Patents and Trademarks